United States Patent
Utagawa et al.

(10) Patent No.: US 9,113,820 B2
(45) Date of Patent: Aug. 25, 2015

(54) IMAGING APPARATUS AND CONTROL METHOD THEREFOR

(71) Applicant: CANON KABUSHIKI KAISHA, Tokyo (JP)

(72) Inventors: Tsutomu Utagawa, Yokohama (JP); Tomoyuki Makihira, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 27 days.

(21) Appl. No.: 13/765,897

(22) Filed: Feb. 13, 2013

(65) Prior Publication Data

US 2013/0215386 A1    Aug. 22, 2013

(30) Foreign Application Priority Data

Feb. 21, 2012    (JP) .................................. 2012-035317

(51) Int. Cl.
*A61B 3/00* (2006.01)
*A61B 3/10* (2006.01)
*A61B 3/12* (2006.01)

(52) U.S. Cl.
CPC ............. *A61B 3/1025* (2013.01); *A61B 3/0008* (2013.01); *A61B 3/12* (2013.01)

(58) Field of Classification Search
CPC .... A61B 3/1225; A61B 3/008; A61B 3/1025; A61B 3/14
USPC ........................................................ 351/221
See application file for complete search history.

(56) References Cited

U.S. PATENT DOCUMENTS

| | | | |
|---|---|---|---|
| 4,387,993 A * | 6/1983 | Adrian ......................... | 356/336 |
| 8,235,528 B2 | 8/2012 | Mukai et al. | |
| 2009/0086164 A1* | 4/2009 | Akita et al. ................... | 351/206 |
| 2010/0277692 A1* | 11/2010 | Mukai et al. .................. | 351/208 |
| 2012/0002166 A1 | 1/2012 | Tomatsu et al. | |
| 2012/0154747 A1 | 6/2012 | Makihira | |
| 2012/0229761 A1 | 9/2012 | Makihira | |
| 2012/0229762 A1 | 9/2012 | Makihira | |
| 2012/0229763 A1 | 9/2012 | Suehira et al. | |
| 2012/0229764 A1 | 9/2012 | Tomatsu et al. | |
| 2012/0229765 A1 | 9/2012 | Makihira | |
| 2012/0287400 A1 | 11/2012 | Utagawa | |
| 2012/0327365 A1 | 12/2012 | Makihira | |
| 2013/0070988 A1 | 3/2013 | Makihira | |

FOREIGN PATENT DOCUMENTS

JP    2010-259543 A    11/2010

* cited by examiner

*Primary Examiner* — Jordan Schwartz
(74) *Attorney, Agent, or Firm* — Fitzpatrick, Cella, Harper & Scinto (57) ABSTRACT

In order to solve the problem in that, when a fundus is irradiated with multiple beams, a load has been placed on a subject, an imaging apparatus for imaging an object to be inspected based on return light from a first area in the object to be inspected, which is irradiated with first light, including: a determination unit for determining a second area being narrower than the first area in the object to be inspected; and a control unit for restricting the irradiation with the first light in the second area, which is irradiated with second light.

13 Claims, 11 Drawing Sheets

IMAGING APPARATUS AND CONTROL METHOD THEREFOR

BACKGROUND OF THE INVENTION

1. Field of the Invention

The present invention relates to an imaging apparatus such as an ophthalmologic apparatus and a control method therefor, and more particularly, to a technology exemplified by a fundus imaging method and apparatus for scanning a fundus with irradiation light to obtain a fundus image.

2. Description of the Related Art

In recent years, as devices for imaging a fundus, the use of a fundus imaging apparatus for scanning with irradiation light to image or photograph the fundus, such as confocal scanning laser ophthalmoscope (SLO) for acquiring a still or moving image of high resolution, has been popular. In such fundus imaging apparatus, in order to image or photograph a narrow area of the fundus in an enlarged manner with high magnification, it is important for an inspector to be able to confirm which part of the fundus is being imaged. (Japanese Patent Application Laid-Open No. 2010-259543).

With the configuration disclosed in Japanese Patent Application Laid-Open No. 2010-259543, in order to acquire a clear fundus image, a subject is irradiated simultaneously with a beam for imaging the entire fundus and a beam for imaging the narrow area of the fundus, and hence a load on the subject has been heavy.

SUMMARY OF THE INVENTION

The present invention is to provide an apparatus and method which enable an inspector to confirm which part of a fundus of a subject is being imaged while suppressing a load on the subject.

In order to achieve the above-mentioned object, according to an exemplary embodiment of the present invention, there is provided an imaging apparatus for imaging an object to be inspected based on return light from a first area in the object to be inspected, which is irradiated with first light, including: a determination unit for determining a second area being narrower than the first area in the object to be inspected; and a control unit for restricting the irradiation with the first light in the second area, which is irradiated with second light.

According to the exemplary embodiment of the present invention, it is possible to enable the inspector to confirm which part of the fundus of the subject is being imaged while suppressing the load on the subject.

Further features of the present invention will become apparent from the following description of exemplary embodiments with reference to the attached drawings.

DESCRIPTION OF THE EMBODIMENTS

Embodiments of the present invention are described in detail with reference to the drawings.

First Embodiment

Now, an ophthalmologic apparatus according to a first embodiment of the present invention, in particular, a fundus imaging apparatus is described.

In this embodiment, description is given of an example in which an apparatus for imaging a wide field of a fundus (hereinafter referred to as wide-field SLO apparatus (WF-SLO apparatus)) is used as a first fundus imaging apparatus, an adaptive optics SLO apparatus (AO-SLO apparatus) is used as a second fundus imaging apparatus, a WF-SLO beam and an AO-SLO beam enter and scan the fundus simultaneously, and a stable and high-quality AO-SLO image is acquired while confirming which area of the fundus is being acquired by the second fundus imaging apparatus with a WF-SLO image acquired by the WF-SLO apparatus.

(Overall Configuration of Apparatus)

Figure 1:
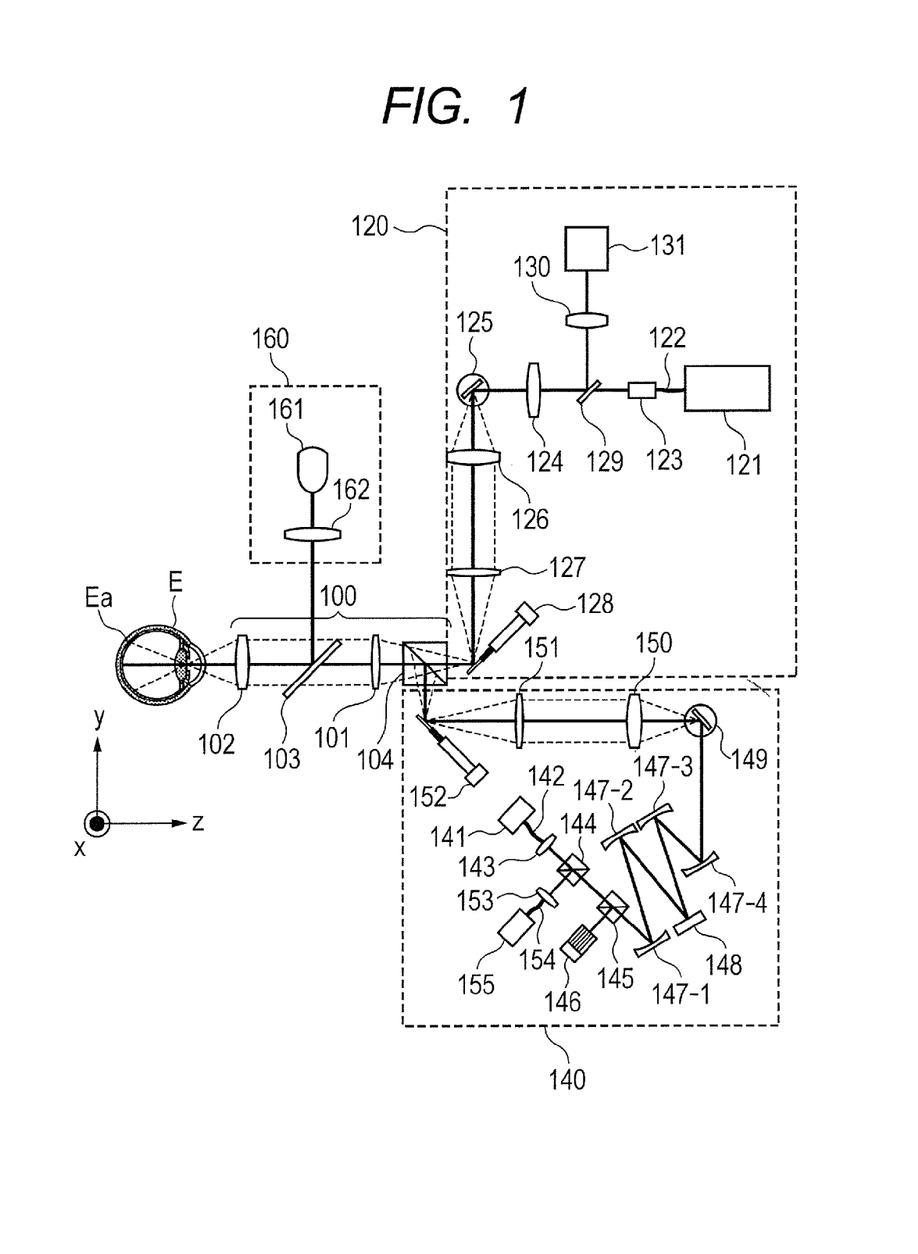
FIG. 1 is a schematic diagram of a configuration of a fundus imaging apparatus according to a first embodiment.

The fundus imaging apparatus according to this embodiment is described with reference to an optical schematic diagram of FIG. 1.

The fundus imaging apparatus used in this embodiment includes the WF-SLO apparatus, the AO-SLO apparatus, and an internal fixation target apparatus.

The WF-SLO apparatus includes an ocular lens unit 100 and a WF-SLO 120. A WF-SLO light source 121 may suitably be a semiconductor laser or a super luminescent diode (SLD) light source. In order to reduce the brightness of a subject and maintain the resolution for fundus observation, the wavelength to be used is suitably a near infrared wavelength range of 700 nm to 1,000 nm. In this embodiment, a semiconductor laser having a wavelength of 780 nm is used. The WF-SLO light source 121 is controlled by a control portion (not shown) to be turned ON/OFF in synchronization with WF-SLO scanners (X) and (Y) and AO-SLO scanners (X) and (Y), which are to be described below. Light emitted from the WF-SLO light source 121 is transmitted through a fiber 122 to be emitted from a fiber collimator 123 as a collimated beam (measuring light). Note that, the measuring light corresponds to a first beam for irradiating an eye to be inspected in the present invention, and the WF-SLO light source corresponds to a first light source in the present invention.

The emitted light is guided to a WF-SLO scanner (X) 128 through a lens 124, a WF-SLO scanner (Y) 125, and relay lenses 126 and 127. The beam is further transmitted through a scan lens 101 and an ocular lens 102 to enter an eye to be inspected E. In this embodiment, galvano scanners are used as the WF-SLO scanners (X) 128 and (Y) 125. Those scanners correspond to a first scanning unit for scanning the first beam over the eye to be inspected in the present invention. Angles of mirrors constituting the WF-SLO scanners (X) 128 and (Y) 125 are controlled by an angular signal output from a control portion (not shown).

Z, x, and y coordinates to be used in this embodiment correspond to an eye axis direction, and a horizontal direction and a vertical direction with respect to a fundus image, respectively. In this embodiment, the x direction corresponds to a main scanning direction, and the y direction corresponds to a sub scanning direction.

The beam that has entered the eye to be inspected E irradiates a fundus Ea of the eye to be inspected E as a spot beam. This beam is reflected or scattered by the fundus Ea of the eye to be inspected E and follows the same optical path to return to a ring mirror 129. Of the light that irradiates the fundus Ea and is back-scattered, the light that has passed through a portion around the pupil (reflected light) is reflected by the ring mirror 129 and received by an avalanche photodiode (hereinafter referred to as APD) 131 through a lens 130.

Similarly to the WF-SLO apparatus, the AO-SLO apparatus includes the ocular lens unit 100 and an AO-SLO unit 140 having an AO function. As an AO-SLO light source 141, an SLD light source having a wavelength of 840 nm is used. In this embodiment, the light source is shared for imaging the fundus and for measuring a wavefront, but a configuration may be adopted in which separate light sources are used and light beams are combined in the course of the optical path.

The light emitted from the AO-SLO light source 141 is transmitted through a fiber 142 to be radiated from a fiber collimator 143 as collimated measuring light. The radiated measuring light is transmitted through a beam splitter 144 and guided to a compensation optical system. The light corresponds to a second beam in the present invention, and the AO-SLO light source corresponds to a second light source in the present invention.

The compensation optical system includes a beam splitter 145, a wavefront sensor 146 for measuring aberration, a wavefront correction device 148, and reflection mirrors 147-1 to 147-4 for guiding the light to those components. The reflection mirrors 147-1 to 147-4 are arranged so that at least the eye to be inspected E and each of the wavefront sensor 146 and the wavefront correction device 148 have an optically conjugate relationship. Further, in this embodiment, a spatial phase modulator using a liquid crystal element is used as the wavefront correction device 148.

The measuring light enters the wavefront correction device 148 to be reflected thereby, and is emitted to the reflection mirror 147-3. Similarly, the light that has returned from the fundus Ea of the eye to be inspected E also enters the wavefront correction device 148, and is then emitted to the reflection mirror 147-2. Further, the measuring light is scanned two-dimensionally by an AO-SLO scanner (X) 149 and an AO-SLO scanner (Y) 152. The beam is transmitted through relay lenses 150, 151 from the AO-SLO scanner (X) 149 to the AO-SLO scanner (Y) 152. Those scanners correspond to a second scanning unit for scanning the second beam over the eye to be inspected in the present invention. In this embodiment, galvano scanners are used as the AO-SLO scanners (X) 149 and (Y) 152. Angles of mirrors constituting the AO-SLO scanners (X) 149 and (Y) 152 are controlled by an angular signal output from a control portion (not shown).

The measuring light scanned by the AO-SLO scanners (X) 149 and (Y) 152 is reflected by a beam splitter 104 and transmitted through the scan lens 101 and the ocular lens 102 to enter the eye to be inspected E. The measuring light that has entered the eye to be inspected E is reflected or scattered by the fundus Ea and follows the same optical path, and the beam splitter 145 allows a part of the measuring light to enter the wavefront sensor 146. The wavefront sensor 146 measures a wavefront of the beam, and a Shack-Hartmann sensor is used as the wavefront sensor 146. A part of the reflected/scattered light that has transmitted through the beam splitter 145 is then reflected by the beam splitter 144 and guided to a light intensity sensor 155 including a photomultiplier tube (PM) through a fiber collimator 153 and a fiber 154.

The guided light is converted to an electric signal in the light intensity sensor 155 and subjected to imaging processing by a control portion (not shown). Then, when the control portion rotates the AO-SLO scanner (X) 149 and the AO-SLO scanner (Y) 152 by a minute angle (which means an angle smaller than a scan angle of the WF-SLO 120), light intensity information from an area to be imaged of the fundus Ea is obtained, and an image is constructed as the fundus image to be displayed on a display device (see FIG. 2) under the control of the control portion.

Further, the wavefront sensor 146 and the wavefront correction device 148 are connected to the control portion. The control portion calculates, based on the wavefront acquired by the measurement result of the wavefront sensor 146, such modulation amount (correction amount) as to correct the wavefront to that without the aberration, and instructs the wavefront correction device 148 to perform the modulation. In this embodiment, a reflective liquid crystal spatial phase modulator of 600×600 pixels is used as the wavefront correction device 148.

An internal fixation target 160 includes a light source 161 and a lens 162. As the light source 161, multiple light emitting diodes (LD) arranged in matrix are used. A turn-on position of the light emitting diodes is changed under the control of the control portion in accordance with the part desired to be imaged. Light from the light source 161 is guided to the eye to be inspected E by a dichroic mirror 103 via the lens 162. The light emitted from the light source 161 is 520 nm, and a desired pattern is displayed by the control portion.

(Functional Configuration)

Figure 2:
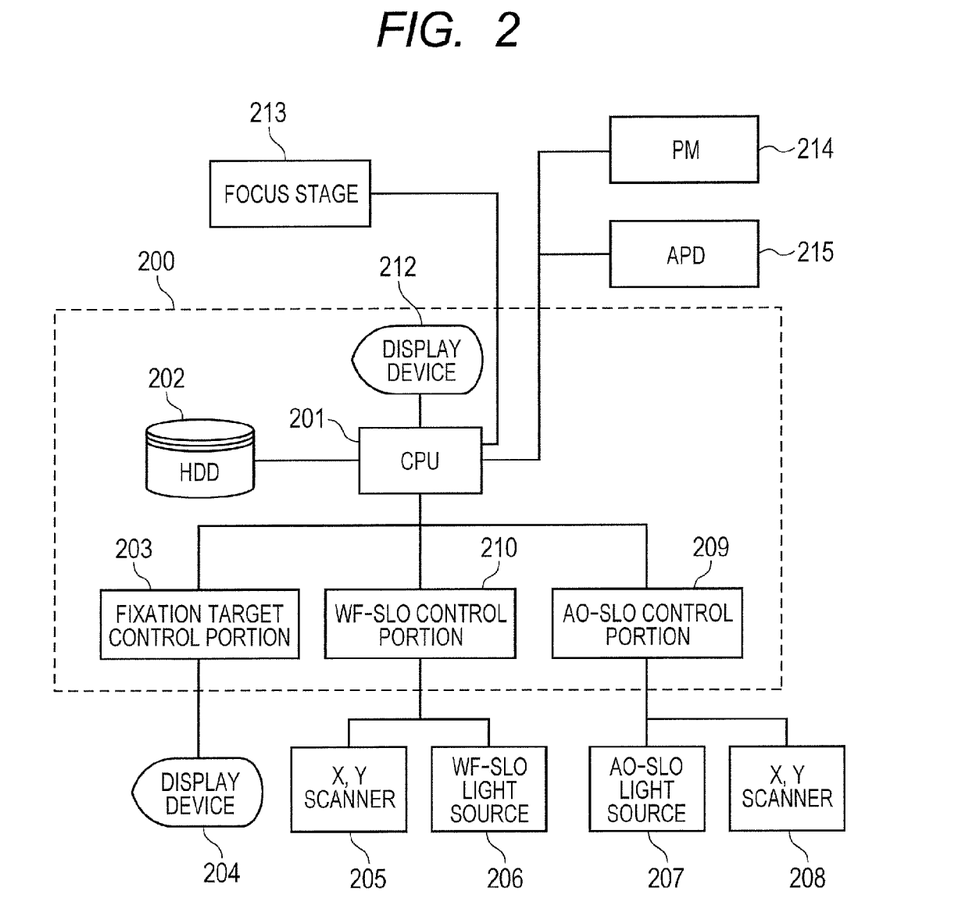
FIG. 2 is a functional schematic diagram of the fundus imaging apparatus according to the first embodiment.

A functional configuration according to this embodiment is described with reference to FIG. 2. A control portion (PC) 200 for controlling functional members includes a display device 212, a CPU 201, a storage device HDD 202, and a fixation target control portion 203, a WF-SLO control portion 210, and an AO-SLO control portion 209, which are control portions for the respective apparatus. Under instructions from the CPU 201, a display device 204 (corresponding to the light source 161 of FIG. 1) for displaying the fixation target, an X, Y scanner 205 (corresponding to the WF-SLO scanners 125 and 128 of FIG. 1) and a WF-SLO light source 206 (corresponding to the WF-SLO light source 121 of FIG. 1) of the WF-SLO apparatus, and an X, Y scanner 208 (corresponding to the AO-SLO scanners 149 and 152 of FIG. 1) and an AO-SLO light source 207 (corresponding to the AO-SLO light source 141 of FIG. 1) of the AO-SLO apparatus are operated under the control of the fixation target control portion 203, the WF-SLO control portion 210, and the AO-SLO control portion 209, respectively. A focus stage 213 is connected to and controlled by the CPU 201.

Further, a signal from the eye to be inspected E is obtained via a PM 214 (corresponding to the light intensity sensor 155 of FIG. 1), which is a light receiving member of the AO-SLO apparatus, and an APD 215 (corresponding to the APD 131 of FIG. 1), which is a light receiving member of the WF-SLO apparatus. The obtained signal is imaged by the CPU 201 and displayed on the display device 212.

(Flow)

Figure 3:
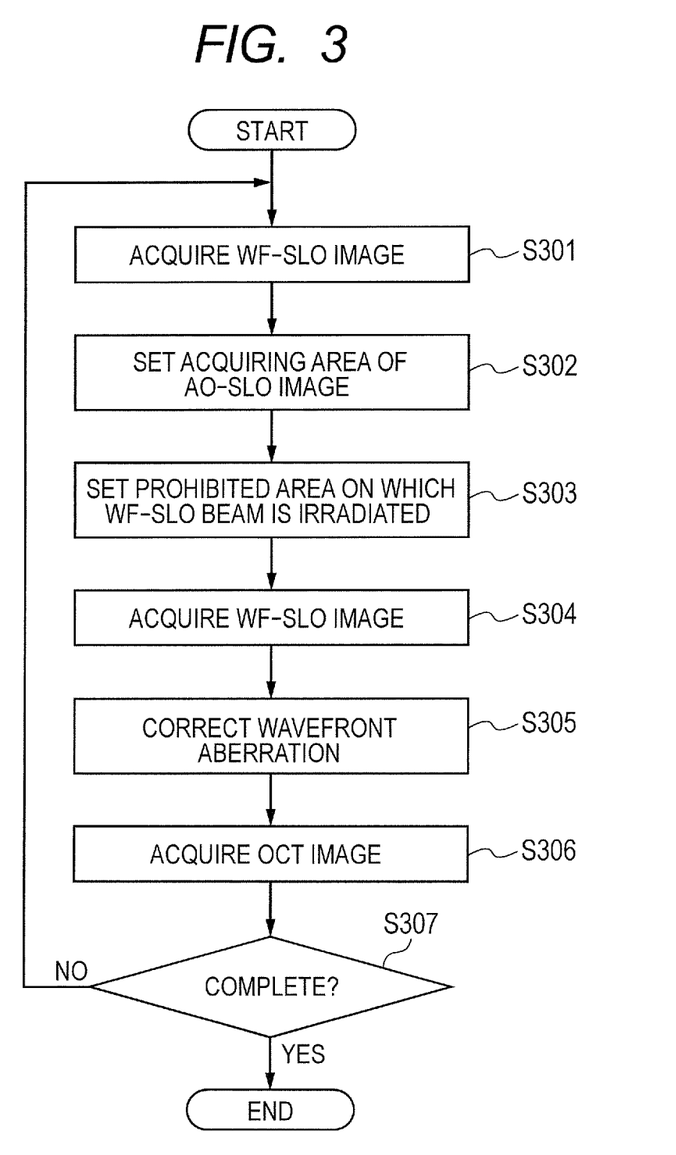
FIG. 3 is a flowchart illustrating the first embodiment.

Now, a method of using the WF-SLO apparatus as the first fundus imaging apparatus and using the AO-SLO apparatus as the second fundus imaging apparatus to acquire an AO-SLO image while confirming an acquiring area of the AO-SLO image with a WF-SLO image is described with reference to a flowchart of FIG. 3. Note that, unless otherwise noted, the processing is executed by the CPU 201.

Figure 4A:
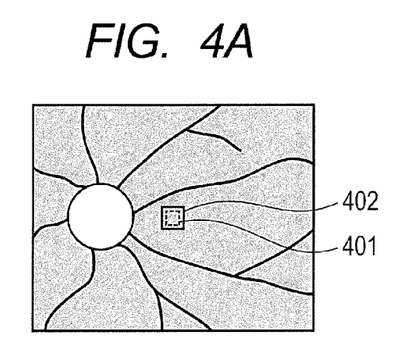
FIG. 4A is a diagram illustrating a state in which an acquiring area of an AO-SLO image is added to a WF-SLO image in the first embodiment.
Figure 4B:
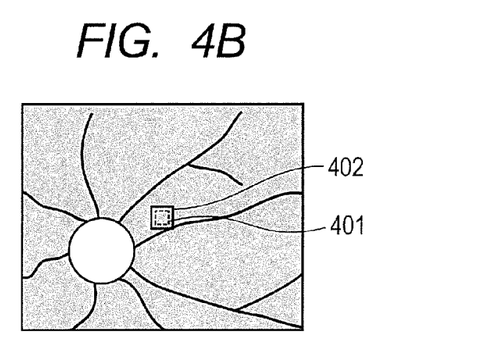
FIG. 4B is a diagram illustrating a state in which the acquiring area is changed from the state illustrated in FIG. 4A.
Figure 4C:
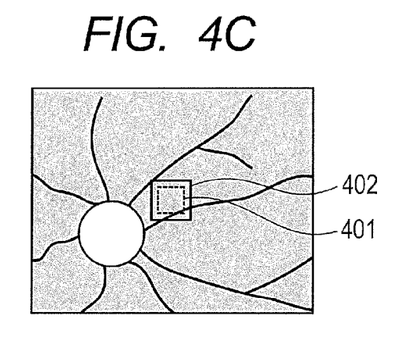
FIG. 4C is a diagram illustrating a state in which a new acquiring area is set from the state illustrated in FIG. 4A.

First, a light emitting diode as a reference of the multiple light emitting diodes arranged in matrix so as to constitute the fixation target 161 is turned on, to thereby visually fix the subject on the fixation target 161. In this state, laser is output from the WF-SLO light source 121 and the reflected light is received by the APD 131 to acquire the WF-SLO image obtained by imaging the wide field of the fundus (Step 301: hereinafter referred to as S301). FIG. 4A is the WF-SLO image acquired in the state in which the light emitting diode as the reference is turned on to visually fix the subject on the fixation target 161. FIGS. 4A to 4C represent the WF-SLO image displayed on the display device 212, to which an acquiring area of the AO-SLO image 401 is added by the CPU 201.

Next, an operator, who is an inspector, selects and turns on a desired light emitting diode from among the multiple light emitting diodes constituting the fixation target 161 via an input device (not shown). When the subject is visually fixed on the turned-on fixation target, the area of which the AO-SLO image is desired to be acquired is centered in the WF-SLO image. FIG. 4B illustrates that when the turned-on position of the fixation target is changed, the acquiring area of the AO-SLO image is changed. Next, the operator specifies the acquiring area of the AO-SLO image via an input device (not shown). FIG. 4C illustrates that an area larger than an initial value is specified as the acquiring area of the AO-SLO image by the operator. Through the above-mentioned operation, the acquiring area of the AO-SLO image, or the area irradiated by the second beam is set (S302).

Next, a certain set range of the acquiring area of the AO-SLO image, which is set in S302, is set as a restricted area of irradiation with the WF-SLO beam (S303). More specifically, an area obtained by adding a predetermined width to the periphery of the acquiring area of the AO-SLO image, which is set in S302, is set as the restricted area of the WF-SLO beam. In this case, the predetermined width is added so as to prevent the WF-SLO beam and the AO-SLO beam from coming close to each other on the fundus. Specifically, in order to reduce the load on the subject, about twice a beam diameter over which the WF-SLO beam irradiates the fundus may be set as the restricted area of the WF-SLO beam. In FIGS. 4A to 4C, the restricted area of the WF-SLO beam is denoted by 402. In this manner, the restricted area of the WF-SLO beam in which the irradiation of the eye to be inspected with the WF-SLO beam as the first beam is prohibited or restricted is set as appropriate based on the irradiation range of the AO-SLO beam as the second beam, and manipulation of the setting is executed by a module area that functions as a unit for setting the restricted area of the WF-SLO beam or a determination unit in the CPU 201.

Next, when the WF-SLO beam is scanned over the restricted area of the WF-SLO beam, which is set in S303, in acquiring the WF-SLO image, the WF-SLO light source 121 is turned off and the WF-SLO image is acquired (S304). The restriction on the irradiation with the first beam is executed by the WF-SLO light source as a first light source, and an instruction to turn off the WF-SLO light source is given by the CPU 201 as a control unit.

Figure 5A:
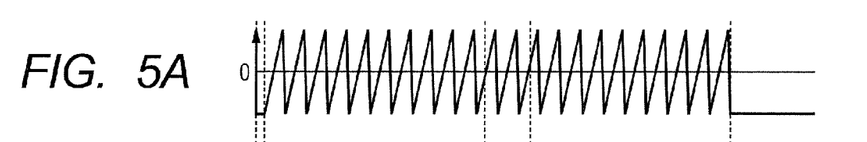
FIGS. 5A, 5B and 5C are graphs showing scanner displacements and a light source ON/OFF state in the first embodiment, respectively.
Figure 5B:
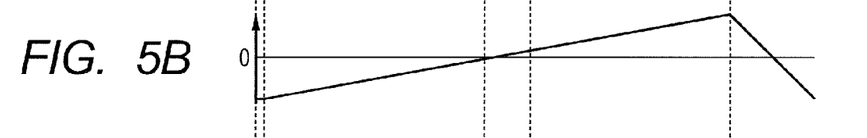
Figure 5C:
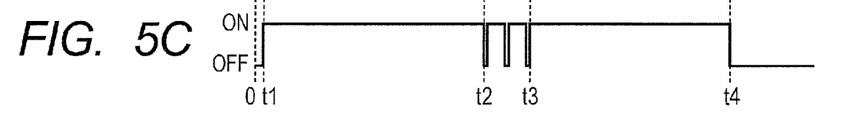

FIGS. 5A to 5C are graphs showing the WF-SLO scanner (X) 128, the WF-SLO scanner (Y) 125, and a turn-on state of the WF-SLO light source 121. The abscissa in FIGS. 5A to 5C represents time. The ordinates in FIGS. 5A and 5B represent displacements (rotational angles) of the WF-SLO scanner (X) 128 and the WF-SLO scanner (Y) 125. FIG. 5C shows the turn-on state of the WF-SLO light source 121. As shown in FIGS. 5A to 5C, when the image acquiring is started at t1, the WF-SLO scanner (X) 128 and the WF-SLO scanner (Y) 125 start rotating in respective periods. Along with the rotations, the WF-SLO light source 121 is turned on. When the WF-SLO scanner (X) 128 and the WF-SLO scanner (Y) 125 reach the restricted area of the WF-SLO beam (interval between t2 and t3 in FIGS. 5A to 5C), the WF-SLO light source 121 is repeatedly turned on/off. In a period from when the WF-SLO scanner (X) 128 and the WF-SLO scanner (Y) 125 reach the outside of the restricted area of the WF-SLO beam to when the image acquiring is complete (interval between t3 and t4 in FIGS. 5A to 5C), the WF-SLO light source 121 is continuously turned on.

Note that, in scanning the WF-SLO beam over the restricted area of the WF-SLO beam, WF-SLO images are continuously acquired with the WF-SLO light source 121 being turned off until the acquisition of the AO-SLO image is complete (S304 to S307). At this time, the most recent WF-SLO image is updated and displayed on the display device 212.

The processing now transitions to the acquisition of the AO-SLO image. First, the light source 141 is turned on in a state in which the AO-SLO scanners 149 and 152 are stopped at center positions. The AO-SLO beam that has irradiated the eye to be inspected E is reflected or scattered by the fundus Ea of the eye to be inspected E and enters the wavefront sensor as reflected or scattered light. The control portion 200 drives the wavefront correction device 148 based on the light that has entered the wavefront sensor and corrects wavefront aberration (S305).

Next, the acquisition of the AO-SLO image is started. The AO-SLO scanners 149 and 152 scan the acquiring area of the AO-SLO image, which is set in S302, with the AO-SLO beam, and return light from the acquiring area of the AO-SLO image is photoelectrically converted by the light intensity sensor 155, with the result that the AO-SLO image is acquired (S306). When the acquisition of the AO-SLO image is complete successfully, the operation may be ended, and when the acquisition of the AO-SLO image is to be continued, the processing may return to S301 to continue the operation of S301 to S306 repeatedly (S307). For example, when the WF-SLO image displayed on the display device 212 has moved, that is, the eye to be inspected has moved in a period from the operation of correcting the wavefront aberration (S305) to the acquisition of the AO-SLO image (S306), the acquisition of the AO-SLO image may be carried out again.

Figure 6A:
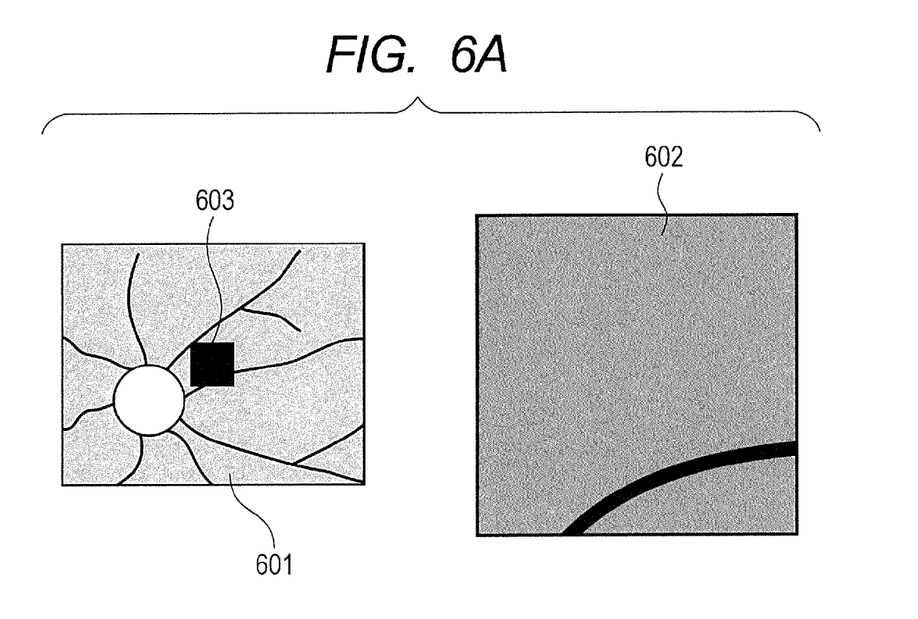
FIGS. 6A and 6B are diagrams illustrating images displayed on a display device according to the first embodiment, respectively.
Figure 6B:
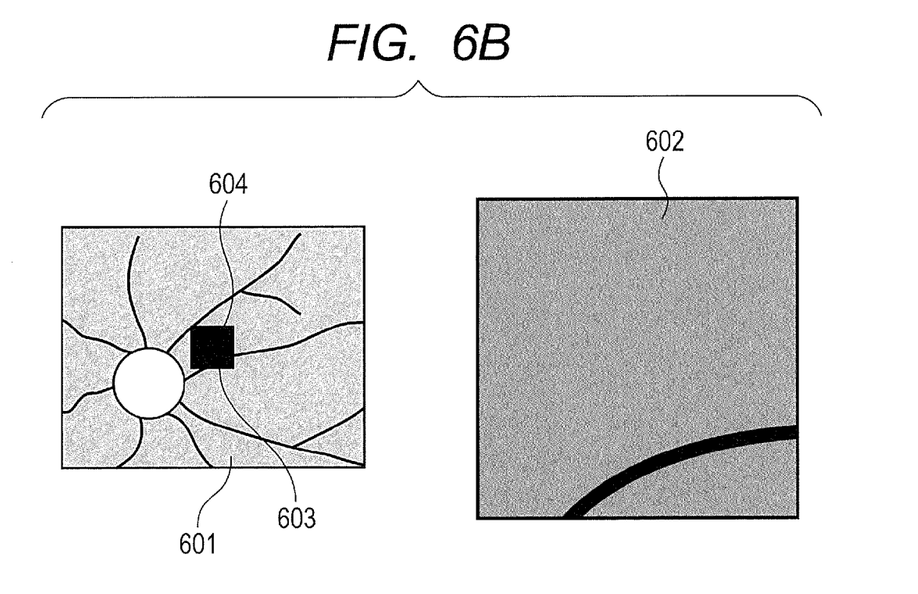

In the above-mentioned embodiment, the case where the acquiring area of the AO-SLO image is added to the WF-SLO image to be displayed has been described. When the WF-SLO beam is turned off in scanning the restricted area of the WF-SLO beam, the restricted area of the WF-SLO beam is imaged as a black area. FIGS. 6A and 6B are diagrams illustrating a real display screen to be displayed on the display device. FIG. 6A illustrates a WF-SLO image 601 and a restricted area of a WF-SLO beam 603. As illustrated in FIG. 6A, the restricted area of the WF-SLO beam is imaged as a black area because the WF-SLO beam does not irradiate the fundus. Therefore, the operator may confirm the acquiring area of the AO-SLO image by just seeing the WF-SLO image. The AO-SLO image is denoted by 602. The operator may observe the appearance of the display screen and confirm whether the AO-SLO image of a desired area is acquired. Further, when it is desired to recognize the acquiring area of the AO-SLO image more accurately, an image in which an acquiring area of an AO-SLO image 604 is added on the WF-SLO image may be displayed as illustrated in FIG. 6B.

Second Embodiment

Now, a second embodiment of the present invention is described.

In this embodiment, description is given of an example in which a WF-SLO apparatus is used as a first fundus imaging apparatus, an optical coherence tomography (OCT) apparatus is used as a second fundus imaging apparatus, a WF-SLO beam and an OCT beam enter and scan the fundus simultaneously, and a stable and high-quality OCT image is acquired while confirming which area of the fundus is being acquired by the second fundus imaging apparatus with a WF-SLO image acquired by the WF-SLO apparatus.

(Overall Configuration of Apparatus)

The fundus imaging apparatus according to this embodiment is described with reference to an optical schematic diagram of FIG. 7.

The first fundus imaging apparatus and the internal fixation target apparatus are similar to those in the first embodiment, and hence description thereof is omitted.

Figure 7:
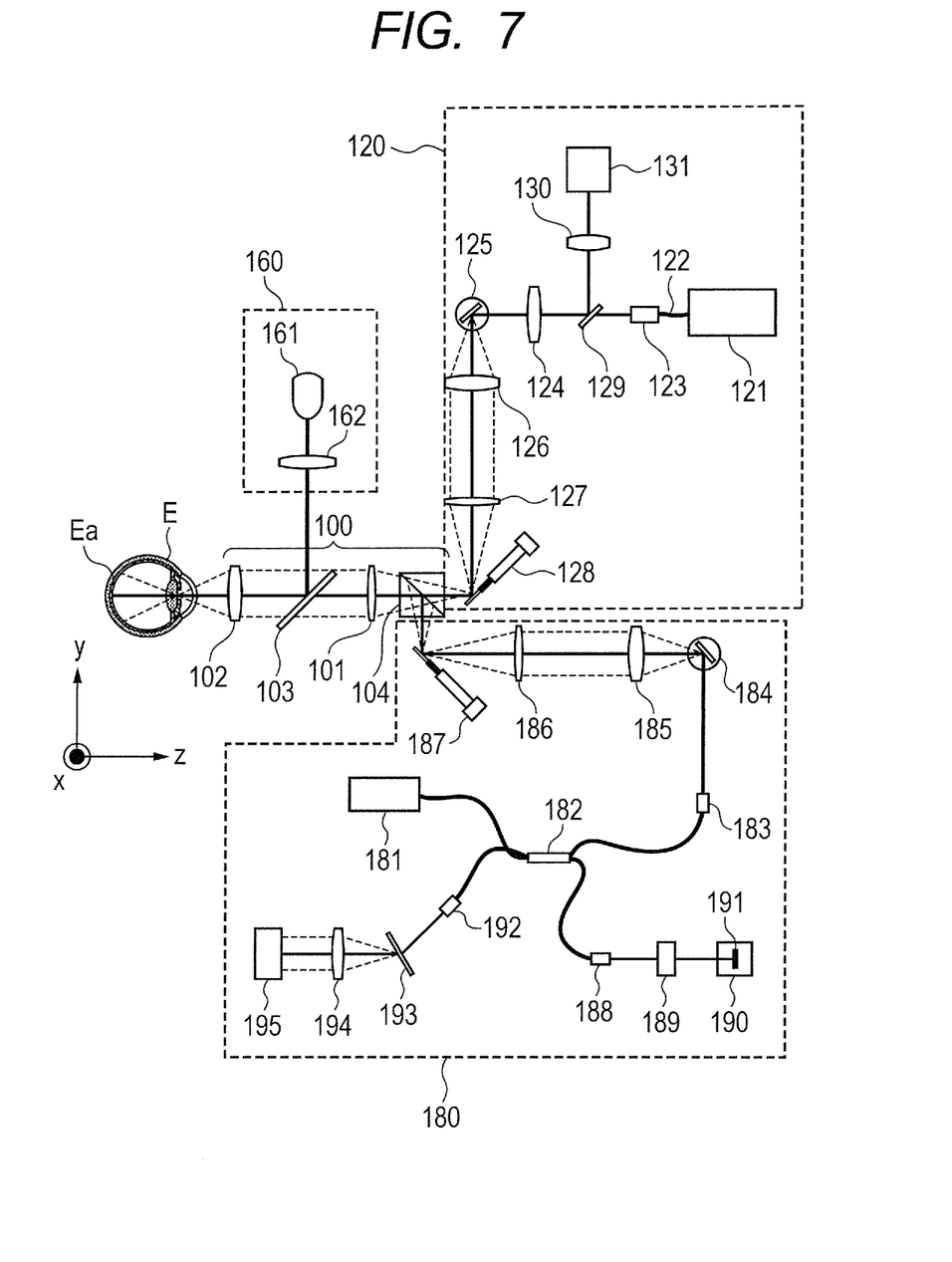
FIG. 7 is a schematic diagram illustrating a configuration of a fundus imaging apparatus according to a second embodiment.

As illustrated in FIG. 7, an OCT apparatus 180 serving as the second fundus imaging apparatus includes a light source 181. As the light source 181, a super luminescent diode (SLD) light source having a center wavelength of 840 nm and a full-width half-maximum wavelength of 45 nm is used. Other than the SLD light source, an amplified spontaneous emission (ASE) light source may suitably be used.

As to the wavelength, wavelengths in the vicinity of 850 nm and 1,050 nm are suitably used for the fundus image acquiring. Low coherent light radiated from the light source 181 is transmitted through a fiber and enters a fiber coupler 182 to be split to measuring light (also referred to as the OCT beam) and reference light. An interferometer configuration using the fiber is described here, but a configuration may be adopted in which a beam splitter is used in a spatial optical system. The measuring light is emitted from a fiber collimator 183 as collimated light.

The measuring light is transmitted through an OCT scanner (Y) 184 and relay lenses 185 and 186, and further through an OCT scanner (X) 187, and enters the eye to be inspected E through the beam splitter 104, the scan lens 101, the dichroic mirror 103, and the ocular lens 102. The beam diameter of the measuring light is about 20 µm at the fundus. In this case, galvano scanners are used as the OCT scanners (X) 187 and (Y) 184.

The measuring light that has entered the eye to be inspected E is reflected by the fundus Ea and follows the same optical path to return to the fiber coupler 182. On the other hand, the reference light is guided from the fiber coupler 182 to a fiber collimator 188 to be radiated as collimated light. The radiated reference light is transmitted through a dispersion compensation glass 189 to be reflected by a reference mirror 191 on a stage with a variable optical path length 190. The reference light reflected by the reference mirror 191 follows the same optical path to return to the fiber coupler 182. The measuring light and the reference light which have returned are combined by the fiber coupler 182 to be guided to a fiber collimator 192. The combined light is hereinafter referred to as interference light.

The fiber collimator 192, a grating 193, a lens 194, and a line sensor 195 constitute a spectrometer. The interference light is measured by the spectrometer as intensity information for each wavelength. The intensity information for each wavelength measured by the line sensor 195 is transferred to a PC (not shown) to form a tomographic image of the fundus Ea of the eye to be inspected E (the phrase "tomographic image" hereinafter indicates a tomographic image of a retina unless otherwise noted).

(Functional Configuration)

Figure 8:
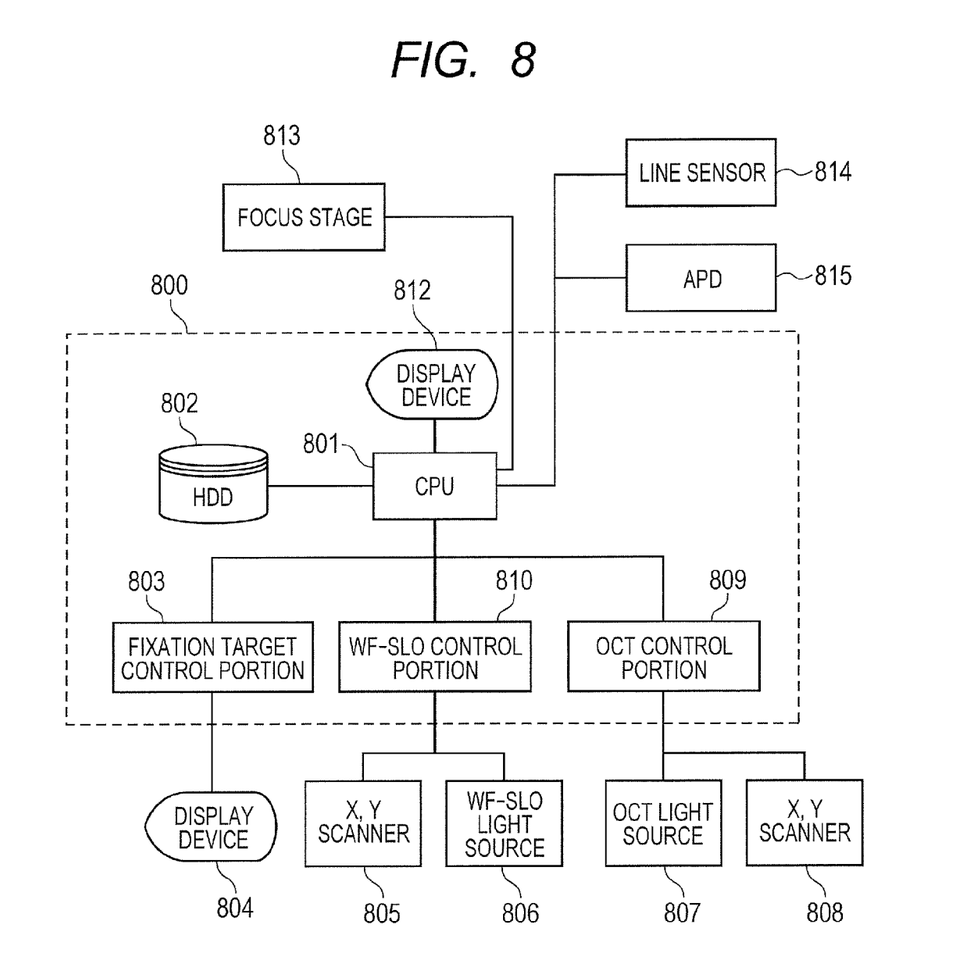
FIG. 8 is a functional schematic diagram of the fundus imaging apparatus according to the second embodiment.

A functional configuration according to this embodiment is described with reference to FIG. 8. A PC 800 for controlling functional members includes a display device 812, a CPU 801, a storage device HDD 802, and a fixation target control portion 803, a WF-SLO control portion 810, and an OCT control portion 809, which are control portions for the respective apparatus. Under instructions from the CPU 801, a display device 804 (corresponding to the light source 161 of FIG. 7) for displaying the fixation target, an X, Y scanner 805 (corresponding to the WF-SLO scanners 125 and 128 of FIG. 7) and a WF-SLO light source 806 (corresponding to the WF-SLO light source 121 of FIG. 7) of the WF-SLO apparatus, and an X, Y scanner 808 (corresponding to the OCT scanners 184 and 187 of FIG. 7) and an OCT light source 807 (corresponding to light source 181 of FIG. 7) of the OCT apparatus are operated under the control of the fixation target control portion 803, the WF-SLO control portion 810, and the OCT control portion 809, respectively.

Further, a signal from the eye to be inspected E is obtained via a line sensor 814 (corresponding to the line sensor 195 of FIG. 7), which is a light receiving member of the OCT apparatus, and an APD 815 (corresponding to the APD 131 of FIG. 7), which is a light receiving member of the WF-SLO apparatus. The obtained signal is imaged by the CPU 801 and displayed on the display device 812. In this embodiment, a first image is a tomographic image of the fundus and a second image is a fundus image.

(Flow)

Figure 9:
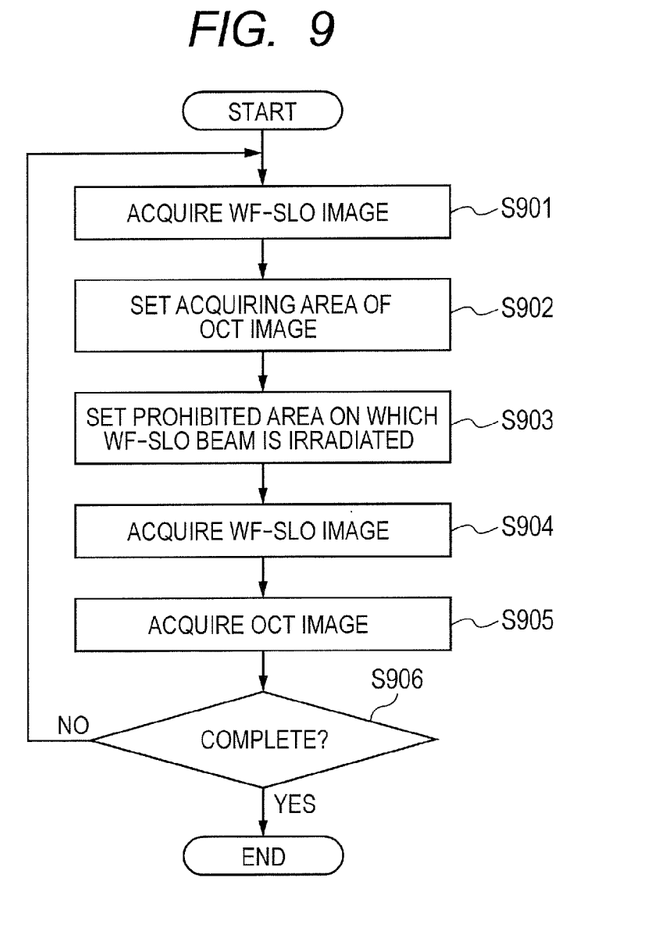
FIG. 9 is a flowchart illustrating the second embodiment.

Now, a method of using the WF-SLO apparatus as the first fundus imaging apparatus and using the OCT apparatus as the second fundus imaging apparatus to acquire an OCT image while confirming an acquiring area of the OCT image with a WF-SLO image is described with reference to a flowchart of FIG. 9. Note that, unless otherwise noted, the processing is executed by the CPU 801.

Figure 10A:
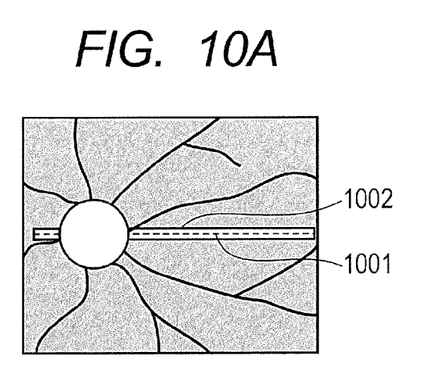
FIG. 10A is a diagram illustrating a state in which an acquiring area of an OCT image is added to a WF-SLO image in the second embodiment.
Figure 10B:
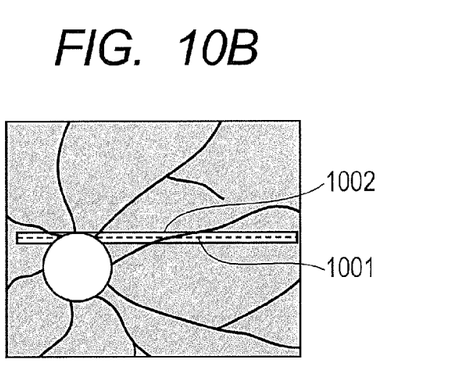
FIG. 10B is a diagram illustrating a state in which a new acquiring area is set from the state illustrated in FIG. 10A.

First, a light emitting diode as a reference of the multiple light emitting diodes arranged in matrix so as to constitute the fixation target 161 is turned on, to thereby visually fix the subject on the fixation target 161. In this state, laser is output from the WF-SLO light source 121 and the reflected light is received by the APD 131 to acquire the WF-SLO image obtained by imaging the wide field of the fundus (Step 901). FIG. 10A is the WF-SLO image acquired in the state in which the light emitting diode as the reference is turned on to visually fix the subject on the fixation target 161. FIGS. 10A and 10B represent the WF-SLO image displayed on the display device 812, to which an acquiring area of the OCT image 1001 is added by the CPU 801.

Next, an operator, who is an inspector, selects and turns on a desired light emitting diode from among the multiple light emitting diodes constituting the fixation target 161 via an input device (not shown). When the subject is visually fixed on the turned-on fixation target, the area of which the OCT image is desired to be acquired is centered in the WF-SLO image, and an acquiring area of the OCT image is thus set. FIG. 10B illustrates that when the turned-on position of the fixation target is changed, the acquiring area of the OCT image is changed.

Next, a certain set range of the acquiring area of the OCT image, which is set in S902, is set as a restricted area of irradiation with the WF-SLO beam (S903). More specifically, an area obtained by adding a predetermined width to the periphery of the acquiring area of the OCT image, which is set in S902, is set as the restricted area of the WF-SLO beam. In this case, the predetermined width is added so as to prevent the WF-SLO beam and the OCT beam from coming close to each other on the fundus. Specifically, in order to reduce the load on the subject, about twice a beam diameter over which the WF-SLO beam irradiates the fundus may be set as the restricted area of the WF-SLO beam. In FIGS. 10A and 10B, the restricted area of the WF-SLO beam is denoted by 1002. Next, when the WF-SLO beam is scanned over the restricted area of the WF-SLO beam, which is set in S903, in acquiring the WF-SLO image, the WF-SLO light source 121 is turned off and the WF-SLO image is acquired (S904). Note that, in scanning the WF-SLO beam over the restricted area of the WF-SLO beam, WF-SLO images are continuously acquired with the WF-SLO light source 121 being turned off until the acquisition of the OCT image is complete (S904 to S906). At this time, the most recent WF-SLO image is updated and displayed on the display device 812.

Next, the acquisition of the OCT image is started. The OCT scanners 184 and 187 scan the acquiring area of the OCT image, which is set in S902, with the OCT beam, and return light from the acquiring area of the OCT image is photoelectrically converted by the line sensor 195, with the result that the OCT image is acquired (S905). When the acquisition of the OCT image is complete successfully, the operation may be ended, and when the acquisition of the OCT image is to be continued, the processing may return to S901 to continue the operation of S901 to S905 repeatedly (S906). For example, when the WF-SLO image displayed on the display device 812 has moved, that is, the eye to be inspected has moved while the OCT image is being acquired (S905), the acquisition of the OCT image may be carried out again.

Another Embodiment

Figure 11:
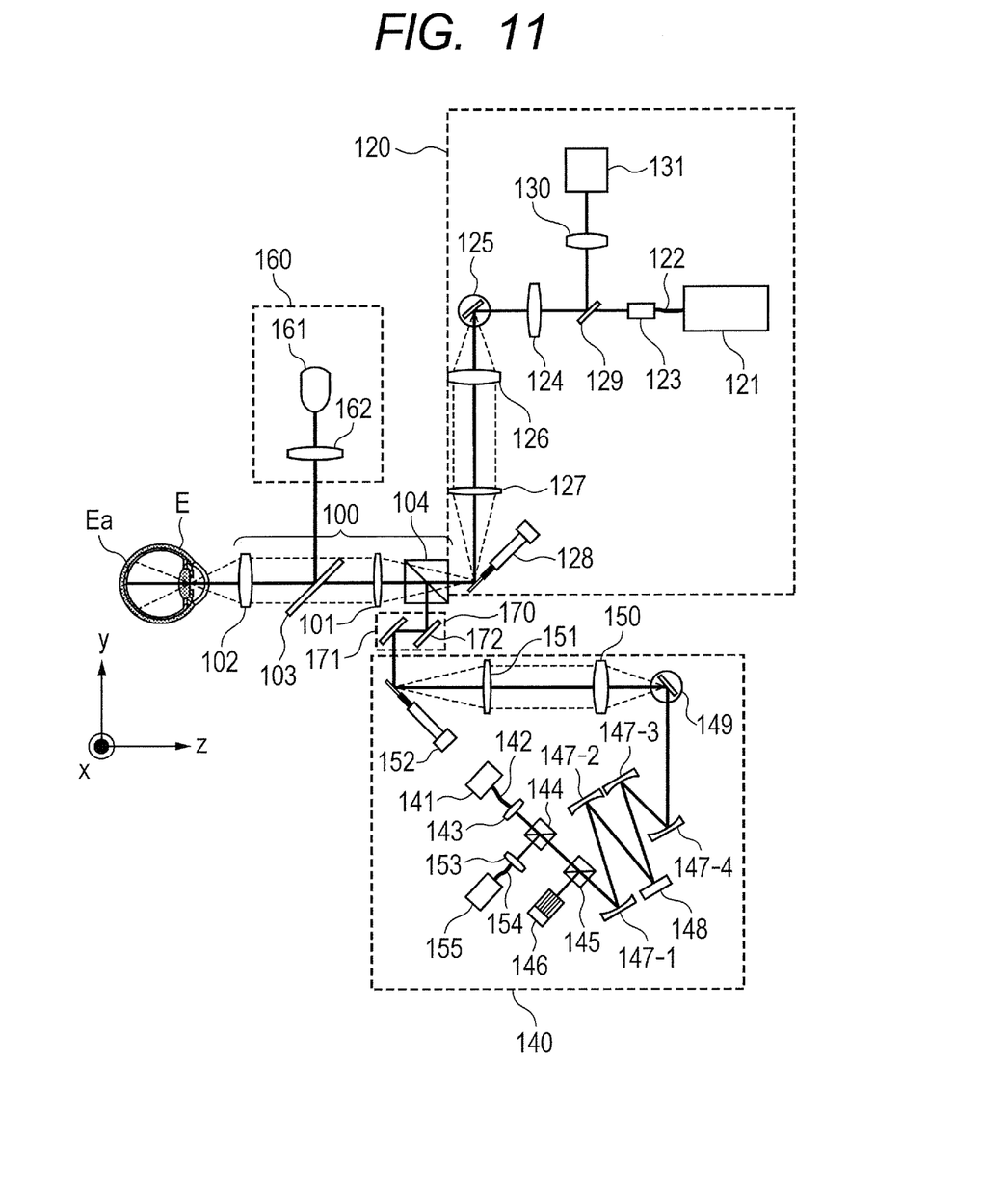
FIG. 11 is a schematic diagram illustrating a configuration of a fundus imaging apparatus according to another embodiment.
Figure 12A:
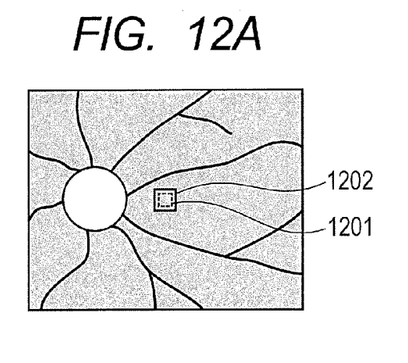
FIG. 12A is a diagram illustrating a state in which an acquiring area of an AO-SLO image is added to a WF-SLO image in the another embodiment.
Figure 12B:
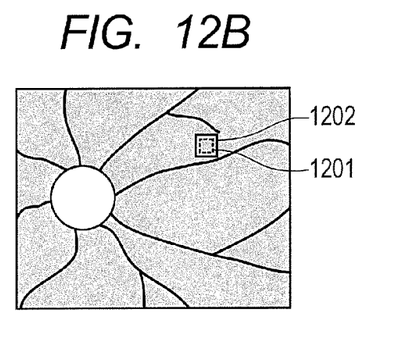
FIG. 12B is a diagram illustrating a state in which a new acquiring area is set from the state illustrated in FIG. 12A.
Figure 13A:
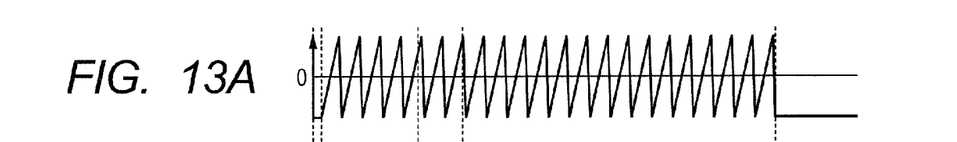
FIGS. 13A, 13B and 13C are graphs showing scanner displacements and a light source ON/OFF state in the another embodiment, respectively.
Figure 13B:
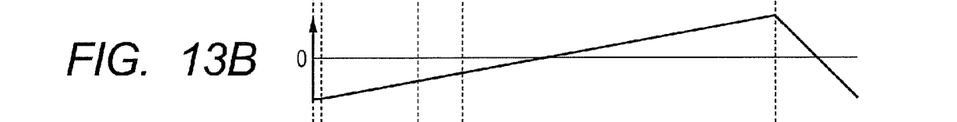
Figure 13C:
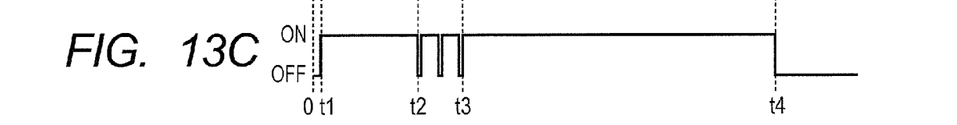

In the first and second embodiments described above, there has been described the configuration in which, by changing the turn-on position of the fixation target to visually fix the subject on the turned-on fixation target, the acquiring area of the AO-SLO image and the acquiring area of the OCT image are always centered in an acquiring area of the WF-SLO image. However, it is also possible to employ a method of turning on the fixation target always at a fixed position and moving the acquiring area of the AO-SLO SLO image. FIG. 11 illustrates a configuration of an apparatus in which the turn-on position of the above-mentioned fixation target is fixed and the acquiring area of the AO-SLO image is moved. The configuration of FIG. 11 is different from the configuration of FIG. 1 in that a unit for changing the acquiring area of the AO-SLO image 170 is provided between the AO-SLO unit 140 and the beam splitter 104. In the unit for changing the acquiring area 170, mirrors 171 and 172, which are controlled by a control portion (not shown) and rotatable with respect to the X axis and the Y axis, respectively, are provided. Each of the mirrors 171 and 172 may rotate to change the position of the fundus Ea to be scanned by the measuring light. FIGS. 12A and 12B are diagrams illustrating a state in which the acquiring area of the AO-SLO image is moved from the center. FIG. 12A indicates that an acquiring area of an AO-SLO image 1201 is located at a center portion of the WF-SLO image. A prohibited area of acquisition of a WF-SLO image is denoted by 1202. FIG. 12B illustrates a state in which the mirrors 171 and 172 in the unit for changing the acquiring area 170 are rotated by the control portion so that a decentered position is set as the acquiring area of the AO-SLO image 1201. FIGS. 13A to 13C are graphs showing the WF-SLO scanner (X) 128, the WF-SLO scanner (Y) 125, and the turn-on state of the WF-SLO light source 121 when the prohibited area of the acquisition of the WF-SLO image 1202 illustrated in FIG. 12B is set. All the ordinates, abscissa, and the like in FIGS. 13A to 13C are the same as those in FIGS. 5A to 5C, and hence description thereof is omitted.

Figure 14:
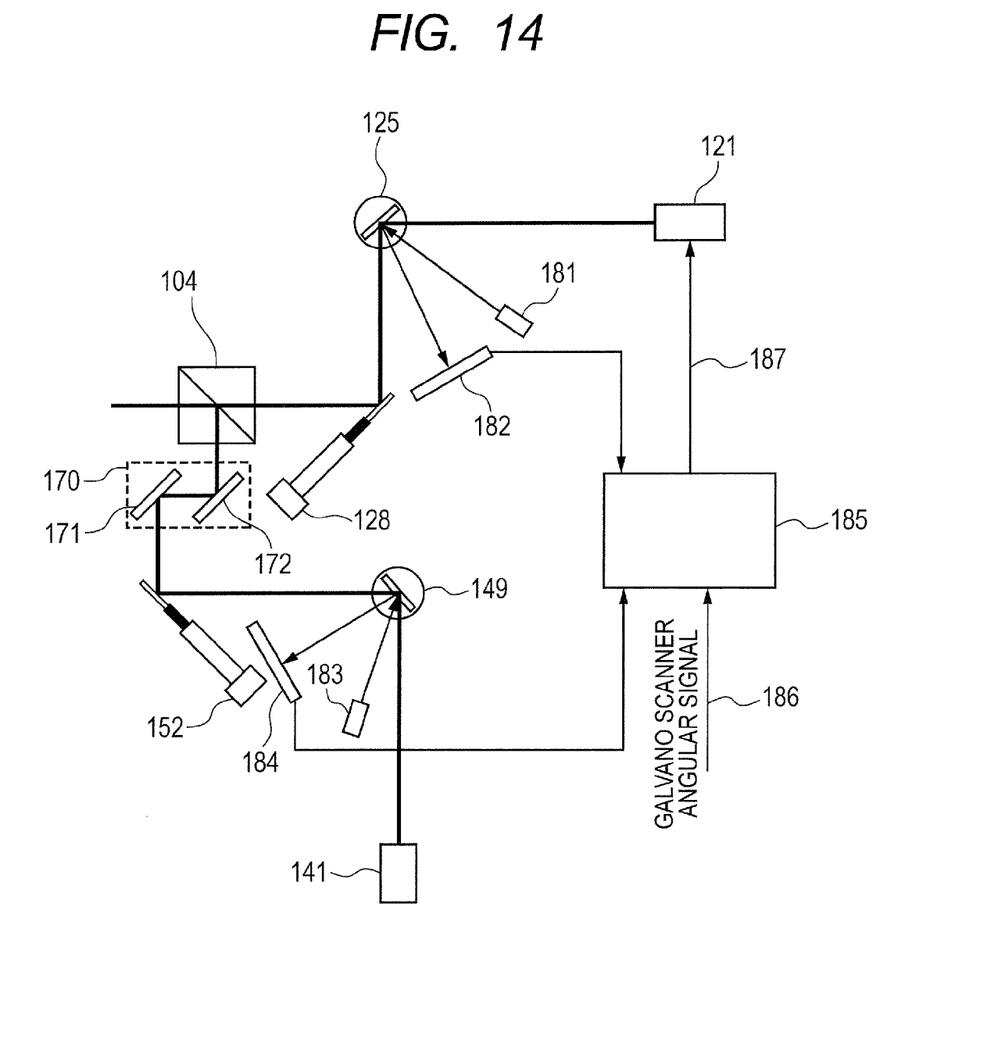
FIG. 14 is a schematic diagram illustrating a partial configuration of the fundus imaging apparatus according to the another embodiment.

In the above-mentioned first embodiment, the method involving using the galvano scanners for all the WF-SLO scanners (X) and (Y) and the AO-SLO scanners (X) and (Y) has been described. Now, description is given of a configuration in which, in order to reduce the imaging time, a resonance scanner is used for each of the WF-SLO scanner (X) and the AO-SLO scanner (X) in the main scanning direction in which high-speed scanning is required. In the galvano scanners, angles of the mirrors are controlled by angular control signals, and hence the control portion can keep track of the mirror positions of the scanners, that is, the irradiation position of the WF-SLO beam and the irradiation position of the AO-SLO beam on the fundus. However, in the resonance scanner, the mirror angle is changed by the resonance of the scanner itself, and hence the control portion cannot keep track of the mirror position. Therefore, when the resonance scanner is used, it is necessary to separately irradiate the mirror of the resonance scanner with a beam such as a laser and convert the light reflected by the mirror into an electric signal by a photoelectric conversion unit such as the line sensor so as to keep track of the mirror angle of the resonance scanner, that is, the irradiation position of each beam on the fundus. Referring to FIG. 14, description is given of a method of keeping track of the mirror angle of the resonance scanner, that is, the irradiation position of each beam on the fundus. FIG. 14 illustrates only an extracted part of the units around the scanners of FIG. 1 that is necessary for describing the configuration. In FIG. 14, description of the same units as those of FIG. 1 is omitted. Units added to the configuration of FIG. 1 are laser light sources including a WF-SLO position detection light source 181 and an AO-SLO position detection light source 183, line sensors 182 and 184 for photoelectrically converting the reflected light of the laser light sources, and a WF-SLO light source control portion 185. Laser light emitted from the WF-SLO position detection light source 181 irradiates the WF-SLO scanner (X) 125, and the light reflected by the WF-SLO scanner (X) 125 irradiates the WF-SLO line sensor 182. An electric circuit (not shown) is connected to the WF-SLO line sensor 182 and processes a line sensor output signal to detect a reflection position of the laser light source, that is, the mirror angle of the WF-SLO scanner. Similarly, laser light emitted from the AO-SLO position detection light source 183 irradiates the AO-SLO scanner (X) 149, and the light reflected by the AO-SLO scanner (X) 149 irradiates the AO-SLO line sensor 184. An electric circuit (not shown) is connected to the AO-SLO line sensor 184 and processes a line sensor output signal to detect a reflection position of the laser light source, that is, the mirror angle of the AO-SLO scanner (X) 149. The detected angles of the WF-SLO scanner (X) 125 and the AO-SLO scanner (X) 149, and angular signals 186 of the WF-SLO scanner (Y) 128 and the AO-SLO scanner (Y) 152 from a control portion (not shown) are input to the WF-SLO light source control portion 185. Based on the input angular signal of each scanner, the WF-SLO light source control portion 185 may output a control signal 187 to the WF-SLO light source 121 so that the WF-SLO beam and the AO-SLO beam do not irradiate the fundus simultaneously, to thereby perform ON/OFF control.

Further, in this embodiment, the method involving turning off the WF-SLO light source so that the WF-SLO beam and the AO-SLO beam, or the WF-SLO beam and the OCT beam do not irradiate the same area on the fundus simultaneously has been described. However, instead of turning off the WF-SLO light source, a configuration in which a shutter or the like blocks the WF-SLO beam so that the WF-SLO beam does not irradiate the same area on the fundus simultaneously with the AO-SLO beam or the OCT beam may also reduce the load on the subject. Further, when the WF-SLO beam and the AO-SLO beam, or the WF-SLO beam and the OCT beam irradiate the same area on the fundus simultaneously, a configuration in which an amount of light of the WF-SLO light source is reduced to the level where no load is placed on the subject may also provide a similar effect. Therefore, it is preferred to define that the scanning of the prohibited area or restricted area with the first beam is performed with darkening of the first beam, which may encompass those embodiment modes.

Further, in the above-mentioned embodiments, the WF-SLO apparatus is used as the configuration for acquiring the fundus image of a wide range, but the apparatus may execute an image acquisition method involving integrating three-dimensional OCT images other than the SLO images in a depth direction. In this case, it is preferred that first light for obtaining an image of a wide area and second light for obtaining a fine image of a narrow area be generated by a common OCT light source in a time division manner, and that the image of a second area, which is the narrow area, be higher in resolution than the image of a first area, which is the wide area. Further, in order to obtain an image of high resolution, such fine image may be obtained by, for example, increasing the accumulation time, reducing the scanning speed of the light, or increasing the number of scans.

Other Embodiments

Further, the present invention can also be realized by performing the following processing. That is, the processing involves supplying software (program) for realizing the functions of the above-mentioned embodiments to a system or an apparatus via a network or various storage media and causing a computer (or a CPU, an MPU, or the like) of the system or the apparatus to read and execute the program.

Note that, the present invention is not limited to the above-mentioned embodiments and can be variously modified or changed without departing from the spirit of the present invention. For example, in the above-mentioned embodiments, the case where an object to be inspected is an eye has been described, but the present invention can also be applied to objects to be measured such as a skin and an organ other than an eye. In this case, the present invention has an embodiment mode as medical equipment such as an endoscope other than an ophthalmologic apparatus. Thus, it is preferred that the present invention be understood as an inspecting apparatus or imaging apparatus exemplified by an ophthalmologic apparatus and the eye to be inspected be understood as an embodiment mode of an object to be inspected.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-035317, filed Feb. 21, 2012, which is hereby incorporated by reference herein in its entirety.

What is claimed is:

1. An imaging apparatus for imaging an object to be inspected based on return light from a first area in the object to be inspected, which first area is irradiated with first light, the imaging apparatus comprising:
   a first light source for emitting the first light for irradiating the object to be inspected in the first area and a second area, the second area being narrower than the first area in the object to be inspected;
   a first scanning unit for scanning the first light in the first area and the second area;
   a second light source, differing from the first light source, for emitting second light for irradiating the object in the second area; and
   a control unit for restricting, when the object to be inspected is irradiated with the first light and the second light simultaneously, the irradiation with the first light in the second area, which is irradiated with the second light during scanning the first light in the first area and the second area.

2. An imaging apparatus according to claim 1, further comprising:
   a second scanning unit for scanning the second light in the second area,
   wherein an image of the object to be inspected is acquired with reflected light from the object to be inspected when the first light and the second light are scanned.

3. An imaging apparatus according to claim 1, wherein the restricting comprises one of (a) turning off the first light and (b) darkening the second area.

4. An imaging apparatus according to claim 1, wherein the control unit provides the restricting by darkening the second area, and
   wherein the control unit controls, in a state in which the first light is darkened, the second light to scan the second area.

5. An imaging apparatus according to claim 1, wherein an image in the first area is obtained and an image in the second area is obtained, and
   wherein a resolution of the image in the second area is higher than a resolution of the image in the first area.

6. An imaging apparatus according to claim 1, wherein the object to be inspected is a fundus of an eye to be inspected, and
   wherein an image is obtained from the second area and comprises an AO-SLO image.

7. A control method for an imaging apparatus for imaging an object to be inspected based on return light from a first area in the object to be inspected, which first area is irradiated with first light, the control method comprising:
    emitting the first light for irradiating the object to be inspected in the first area and a second area, the second area being narrower than the first area in the object to be inspected;
    scanning the first light in the first area and the second area;
    emitting second light for irradiating the object in the second area, the second light being different from the first light; and
    restricting, when the object to be inspected is irradiated with the first light and the second light simultaneously, the irradiation with the first light in the second area, which is irradiated with the second light during scanning the first light in the first area and the second area.

8. A control method for an imaging apparatus according to claim 7, further comprising:
    scanning the second light in the second area,
    wherein an image of the object to be inspected is acquired with reflected light from the object to be inspected when the first light and the second light are scanned.

9. A control method for an imaging apparatus according to claim 7, wherein the restricting comprises one of (a) turning off the first light and (b) darkening the second area.

10. A control method for an imaging apparatus according to claim 7, wherein the restricting comprises darkening the second area, and
    wherein, in a state in which the first light is darkened, the second light is controlled to scan the second area.

11. A control method for an imaging apparatus according to claim 7, wherein an image in the first area is obtained and an image in the second area is obtained, and
    wherein a resolution of the image in the second area is higher than a resolution of the image in the first area.

12. A control method for an imaging apparatus according to claim 7, wherein the object to be inspected is a fundus of an eye to be inspected, and
    wherein an image is obtained from the second area and comprises an AO-SLO image.

13. A program for causing a computer to execute the steps of the control method for an imaging apparatus according to claim 7.

* * * * *